US006605644B2

(12) United States Patent
Kamin et al.

(10) Patent No.: US 6,605,644 B2
(45) Date of Patent: *Aug. 12, 2003

(54) ANALGESIC REGIMEN

(75) Inventors: Marc Kamin, West Windsor, NJ (US); William Olson, Princeton, NJ (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/002,249

(22) Filed: Oct. 26, 2001

(65) Prior Publication Data

US 2002/0055544 A1 May 9, 2002

Related U.S. Application Data

(63) Continuation of application No. 09/415,753, filed on Oct. 12, 1999, now Pat. No. 6,339,105.

(51) Int. Cl.$^7$ .............................................. A61K 31/135
(52) U.S. Cl. ....................................................... 514/646
(58) Field of Search ......................................... 514/646

(56) References Cited

U.S. PATENT DOCUMENTS

| 3,652,589 | A | * | 3/1972 | Flick et al. | ............... | 260/326 T |
| 5,672,360 | A | * | 9/1997 | Sackler et al. | ............... | 424/490 |
| 6,339,105 | B1 | * | 1/2002 | Kamin et al. | ............... | 514/646 |

FOREIGN PATENT DOCUMENTS

WO            99/23513 A1     11/2000

OTHER PUBLICATIONS

Merck Index (12th Ed) Entry Tramadul (Ultram) Analgesic, Flick et al. US. 3652589, 19772, 1996.*
Katz Today's Therapeutic Trends 31:177–186 (see pp. 180 181 182 183 184) Initiating Tramodol Therapy at a Dose of 25–50 mg. Daily for the First 2–3 Days Reduces Incidence of Nausea, 1995.*
Barkin Formulary 30(9): 542–543 (Tramadol Alternative Dosage Regimen, to Decrease Nausea/Vomiting and Other Side Effects, Day 1—25mg @ 4 Hr While Awake, Day 2—50mg @ 8 Hrs Day 3 50mg @ 6 Hrs While Awake—Slow Titration—Children Over 10—25mg Every 8 Hours, 1995.*
Schnitzer, Kamin & Olson Arthritis Rheum. 42(7):1370–1377 ISSN: 0004–3591, 1999.*
Petrone, Kamin & Olson J. Clin. Pharm. Ther. 24(2):115–123 ISSN: 0269–4727, 1999.*
Ruoff Pharmacotherapy 19(1):88–93 ISSN: 0277–0008, Jan. 1999.*
Sindrup et al Pain 83(1):85–90 ISSN:0304–3959, 1999.*
Gobel et al Drugs 53/Suppl 2:34–39 ISSN: 0012–6667, 1997.*
Lehmann Drugs 53/Suppl 2:25–33 ISSN: 0012–6667, 1997.*
Katz Drugs 52(Suppl 3): 39–47 ISSN: 0012–6667, 1996.*
Budd Rev. Contemp Pharmacothera 6(10):507–512 ISSN: 0954–8602, 1995.*
Ravck Current. Therapeutic Research. 55(12):1417–1431 ISSN: 0011–393X, 1994.*
Luczak Nowotwory 44/4:317–323 ISSN: 0029–540X, 1994.*
International Pharmacy Journal 10(6): 225–227 ISSN: 1010–0423, 1996.*
U.S. 5672360 Sep. 1997.*
Hungarian Novelty Search Report for application No. P0104260 dated Nov. 5, 2002.
Barkin et al.: "Alternative dosing for tramadol aids effectiveness" Formulary, vol. 30, No. 9, 1995, pp. 542–543, XP000874395 the whole document.
Katz et al. "The role of tramadol in the management of musculoskeletal pain" Today's Therap. Trends, vol. 13, No. 3, 1995, pp. 177–186, XP000874368 p. 180 p. 184.
Petrone D et al. "Slowing the titration rate of #tramadol# HC1 reduces the incidence of discontinuation due to nausea and/or vomiting: a double–blind radomized trial" J Clin Pharm Ther, Apr 1999, 24(2) P115–23, XP000869773 England the whole document.
Ruoff Ge: "Slowing the initial titration rate of #tramadol# improves tolerability" Pharmacotherapy, Jan 1999, 19(1) P88–93, XP000869656 United States the whole document.
Taniguchi G. Et al.: "Criteria for use of #tramadol# hydrochloride in adult impatients and outpatients" American Journal of Health–System Pharmacy (Am. J. Health–Syst. Pharm) 1997, 54/6(696–697), XP000869770 United States the whole document.
Katz Wa: "Pharmacology and clinical experience with #tramadol# in osteoarthritis" Drugs, 1996, 52 Suppl 3 P39–47, XP000869774 New Zealand abstract p. 41, left hand column, paragraph 4 p. 42–p. 44.
Cherny N.I.: "Opioid analgesics. Comparatove features and prescribing guidelines" Drugs (drugs—, 1996, 51/5 (713–737), XP000869772 New Zealand p. 717, right–hand column, paragraph 2.6–p. 718, left–hand column, paragraphs 1,2 p. 727, right hand column–page 728 left–hand column, paragraphs 1,2.
Schnitzer, Kamin & Olson Arthritis Pharm. 42(7):1370–1377 ISN:0004–3591, 1999.
Sindrup et al, Pain 83(1) :85–90 ISSN:0304–3959 1999.
Gobel et al, Drugs 53/Suppl 2:34–39 ISSN:0012–6667 1997.
Lehmann; Drugs 53/Suppl 2:25–33 ISSN:0012–6667 1997.
Budd, Rev. Contemp Pharmaco Thera 6(10) :507–512 ISSN:0954–8602 1995.
Ravck Current Therapeutic Research, 55(12) :1417–1431 ISSN:0011–393x 1994.
Luczak, Nowotwory 44/4:317–323 ISSN:0029–540x.
International Pharmacy Journal 10(6):225–227 issn:1010–0423 1996.

* cited by examiner

*Primary Examiner*—Shep K. Rose
(74) *Attorney, Agent, or Firm*—Ralph R. Polo

(57) ABSTRACT

A regimen for the administration of tramadol for the treatment of analgesia is described. The regimen involves a slower initial titration rate of tramadol which results in a significantly lower percentage of discontinuations of therapy due to a lower incidence and severity of side effects.

11 Claims, 5 Drawing Sheets

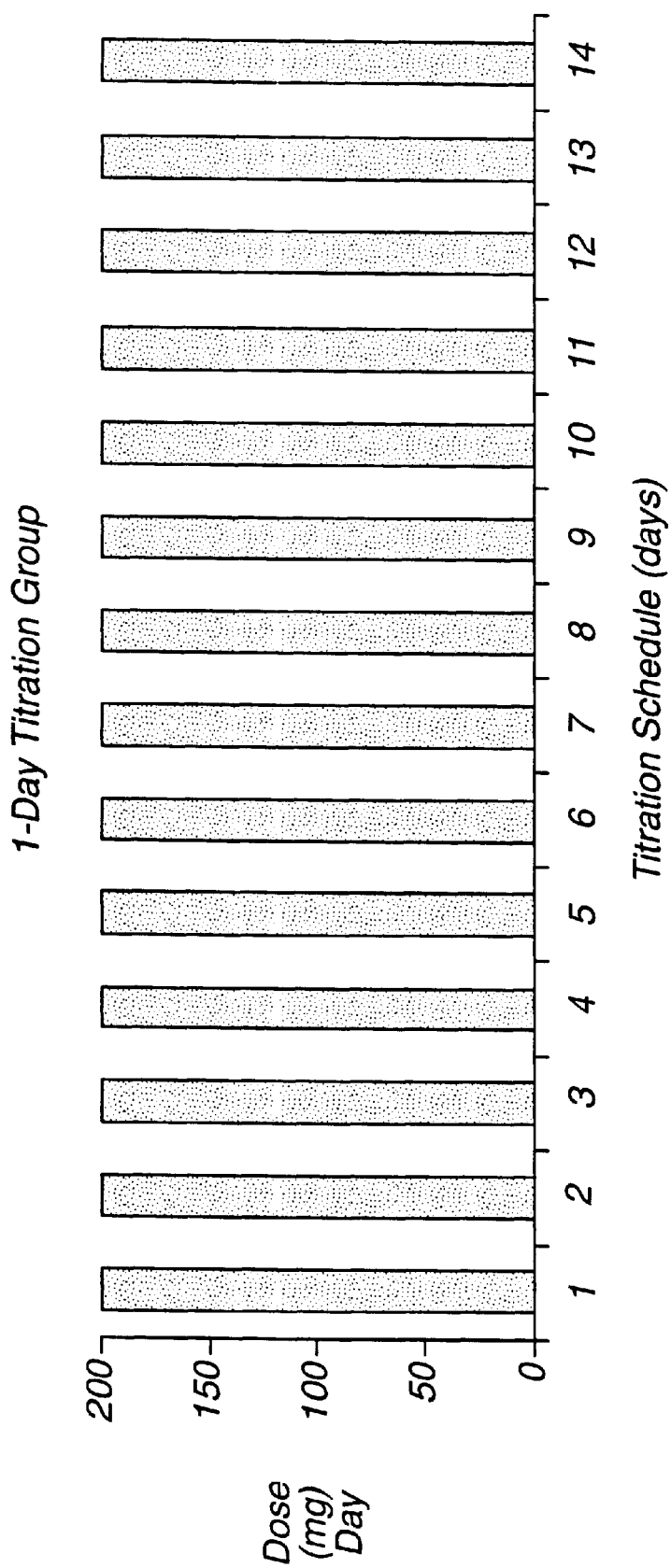

ANALGESIC REGIMEN

Figure 1B:
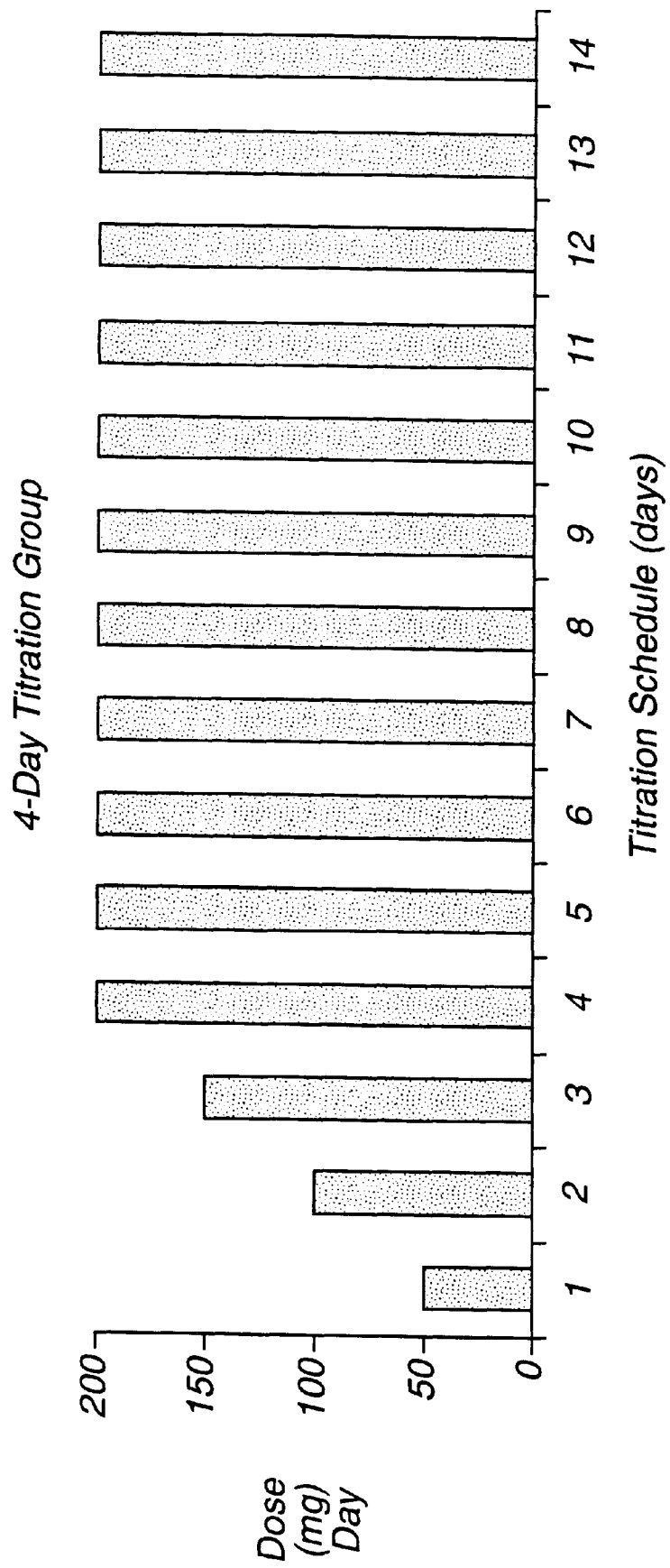

This is a continuation of application Ser. No. 0/41,753, filed Oct. 12, 1999, now U.S. Pat. No. 6,339,105.

FIELD OF THE INVENTION

This invention relates to a dosing regimen for the administration of the analgesic tramadol. The dosing regimen achieves the desired analgesic effect while reducing or delaying the on-set of the side effects generally associated with the administration of tramadol.

BACKGROUND OF THE INVENTION

Tramadol, the chemical name for which is 2-[(dimethylamino)methyl]-1-(3-methoxyphenyl) cyclohexanol, is a synthetic, centrally-acting analgesic that is effective for the treatment of moderate to moderately-severe chronic pain. It has been marketed under the trade name Tramal™ since 1977 in the dosage forms of capsules, injections, suppositories and drops. The compound can be employed as the free base or its pharmaceutically acceptable salts, stereo isomers and solvates. It is generally supplied in the form of its hydrochloride salt and over 400 million doses of tramadol have been administered since its introduction in Germany.

Patients experiencing chronic pain require an analgesic therapeutic regimen that is both effective and well tolerated. The two traditional categories of analgesics, i.e. opioids and nonsteroidal anti-inflammatory drugs (NSAIDs), are both effective but are associated with potentially serious side effects. Concerns regarding tolerance and dependence minimize the chronic use of narcotics such as morphine and codeine for the treatment of chronic pain. Patients on chronic NSAID therapy risk severe gastrointestinal symptoms, including ulceration and bleeding which have been estimated to result in up to 20,000 deaths each year. An alternative to this dilemma is tramadol, a non-narcotic, non-NSAID analgesic which is indicated for the management of moderate to moderately-severe pain.

After oral administration, tramadol is rapidly and almost completely absorbed and is extensively metabolized. The major metabolic pathways appear to be N- and O-demethylation and glucuronidation or sulfation in the liver. Only one metabolite, i.e. mono-O-desmethyltramadol, has been found to be pharmacologically active.

After a single 100 mg oral dose in healthy subjects, peak plasma concentrations of tramadol hydrochloride occurring two hours after administration are 308±78 ng/ml mean±standard deviation). Peak plasma concentrations of mono-O-desmethyl tramadol, the active metabolite of tramadol, are 55±20 ng/ml, occurring approximately three hours after administration. The terminal plasma elimination half-lives of tramadol hydrochloride and its active metabolite are 6.3±11.4 hours and 7.4±1.4 hours respectively. Tramadol is poorly bound to plasma proteins (20.2%) thus decreasing the potential for drug interactions with highly protein-bound agents.

The mode of action of tramadol is not completely understood, but in animal models at least two complementary mechanisms appear to be involved and they are 1) weak binding to the $\mu$ opioid receptors and 2) weak inhibition of the reuptake of norepinephrine and serotonin. Tramadol is not chemically related to opiates, but its actions are similar to those of opioid (narcotic) analgesics. The opioid activity of tramadol results from the low-affinity binding of tramadol hydrochloride and the higher affinity binding of the metabolite to $\mu$ receptors; however, its induced antinociception is only partially antagonized by the opiate antagonist naloxone in several animal tests. The inhibition of norepinephrine and serotonin reuptake, which has been demonstrated in vitro, is postulated to contribute independently to the overall analgesic profile of tramadol hydrochloride.

Tramadol is well tolerated, however, nuisance adverse events such as drowsiness, vomiting and dizziness can occur during the initiation of treatment which may lead to early discontinuation of the treatment. The most frequently reported adverse events observed in clinical trials of tramadol hydrochloride are constipation, nausea, dizziness/vertigo, headache, somnolence, and vomiting. Taken together, the efficacy, safety, and pharmacokinetic profile of tramadol hydrochloride indicate that the drug may be useful in treating chronic pain.

An object of the present invention is to demonstrate that the frequency of nausea and vomiting, two of the most frequently reported adverse events and the events most commonly associated with discontinuation of treatment, as well other adverse events, can be reduced using a lower dosage titration scheme without diminishing the efficacy of the compound.

The present invention relates to a dosage regimen which consists of slowing the titration rate for tramadol which results in a reduction of the incidence of discontinuation due to side effects such as nausea and vomiting.

SUMMARY OF THE INVENTION

The present invention relates to a dosage regimen for tramadol which involves a slower titration rate than that currently prescribed. The slower rate of titration of tramadol therapy results in improved tolerability of the drug. The novel regimen results in a significant reduction in discontinuations due to a lower incidence or severity of side effects. As used hereinafter, the word tramadol is intended to include its pharmaceutically acceptable salts, stereo isomers and solvates thereof.

DETAILED DESCRIPTION OF THE INVENTION

Tramadol is indicated for the treatment of moderate to moderately-severe pain and its typical dosing regimen is 50–100 mg every 4 to 6 hours. About 200 mg/day is considered to be a normal initial dose. Clinical studies have shown tramadol to be an effective treatment for chronic joint pain. Tramadol is well tolerated, however, nuisance adverse events can occur during initiation of treatment with tramadol. These side effects may lead to early discontinuation of tramadol therapy.

Slow titration of a therapeutic agent is often used by practicing clinicians to minimize adverse events associated with centrally-acting agents such as antidepressants, analgesics and anticonvulsants. Although slow titration may minimize the adverse side effects associated with a particular agent, it may also delay the onset of the effect of the agent as well. It has now been discovered that initiating tramadol therapy using slow titration rates according to the regimen of this invention minimizes discontinuations due to adverse side effects associated with tramadol while maintaining its therapeutic effectiveness which results in a greater tolerance of the drug during therapy.

The regimen which is the basis of the present invention is a 1–28 day regimen. In practice, tramadol is administered over a ten-28 day period starting on day one in a pharmaceutical composition containing from about 10–50 mg of tramadol and the amount of drug is increased incrementally over the next 9–28 days until the target dose of about 200–400 mg/day is reached. Many patients find effective pain relief at 200 mg/day, however, some patients may require doses of up to 400 mg/day in order to achieve the desired relief. Generally, on days 1–3 of the regimen tramadol, in the form of the free base or its pharmaceutically acceptable salt, is administered at a dose of about 10–50 mg. On days 4–6 of the regimen tramadol is administered at a dose in the range of about 20–100 mg. On days 7–9 tramadol is administered at a dose in the range of about 30–150 mg and on days 10–28 and thereafter at a dose of about 40–400 mg. At the end of the period the therapy is continued at the target dose which may be anywhere from 200 to about 400 mg of tramadol.

In a preferred embodiment of the invention tramadol is administered in a regimen which comprises administering tramadol at the rate of about 25 mg of tramadol on days 1–3; 50 mg of tramadol on days 4–6; 75 mg of tramadol on days 7–9; 100 mg of tramadol on days 10–12; 150 mg of tramadol on days 13–15; and 200 mg of tramadol on days 16–28 and thereafter.

In another preferred embodiment of the invention tramadol is administered in a regimen which comprises administering tramadol at the rate of 50 mg of tramadol on days 1–3; 100 mg of tramadol on days 4–6; 150 mg of tramadol on days 7–9; and 200 mg of tramadol on day 10 and thereafter.

The drug is generally administered in the form of its pharmaceutically salt. Suitable pharmaceutically acceptable salts include salts of inorganic acids such as hydrochloric and hydrobromic acid. The preferred salt is the hydrochloride salt.

The slower initial titration rate of tramadol is effective in reducing discontinuations due to adverse effects while maintaining the analgesic properties of the compound. This is particularly true in the case of patients who previously had difficulty tolerating an analgesic because of side effects such as nausea and/or vomiting. This result is based on the cumulative proportion of patients who discontinued use of the agent due to adverse side effects.

The following examples describe the invention in greater detail and are intended to illustrate the invention but not to limit it.

EXAMPLE 1

Tramadol, in the form of its hydrochloride salt, was studied in a multicenter, outpatient, randomized, double-blind parallel study that compared the effect of different titration rates of tramadol versus placebo on the incidence of discontinuations resulting from adverse events in patients with chronic joint pain.

A total of 465 patients with chronic joint pain were enrolled in the study and randomized into one of four treatment groups for 14 days. Patients continued on their prestudy dose of NSAIDs while concurrently receiving tramadol or placebo. Tramadol groups were titrated at three different rates to achieve the study target dose of 200 mg/day. Each group was examined to determine if a slower titration resulted in a statistically significant (p<0.05) trend towards fewer discontinuations due to nausea and/or vomiting and dizziness and/or vertigo. Discontinuation due to any adverse event was similarly analyzed. If the trend was statistically significant, pairwise comparisons were performed to determine the statistical significance between titration rates.

The study protocol was approved by an Institutional Review Board at each study site and informed consent regarding the risks and benefits of participation was obtained for all patients. Patients who were (1) 45 years of age or older; (2) had a diagnosis of symptomatic chronic joint pain, as confirmed by x-ray; (3) were in otherwise good general health; (4) were on a stable dose of NSAID for at least 30 days; and (5) required additional pain relief were eligible to enroll in the study.

Figure 1C:
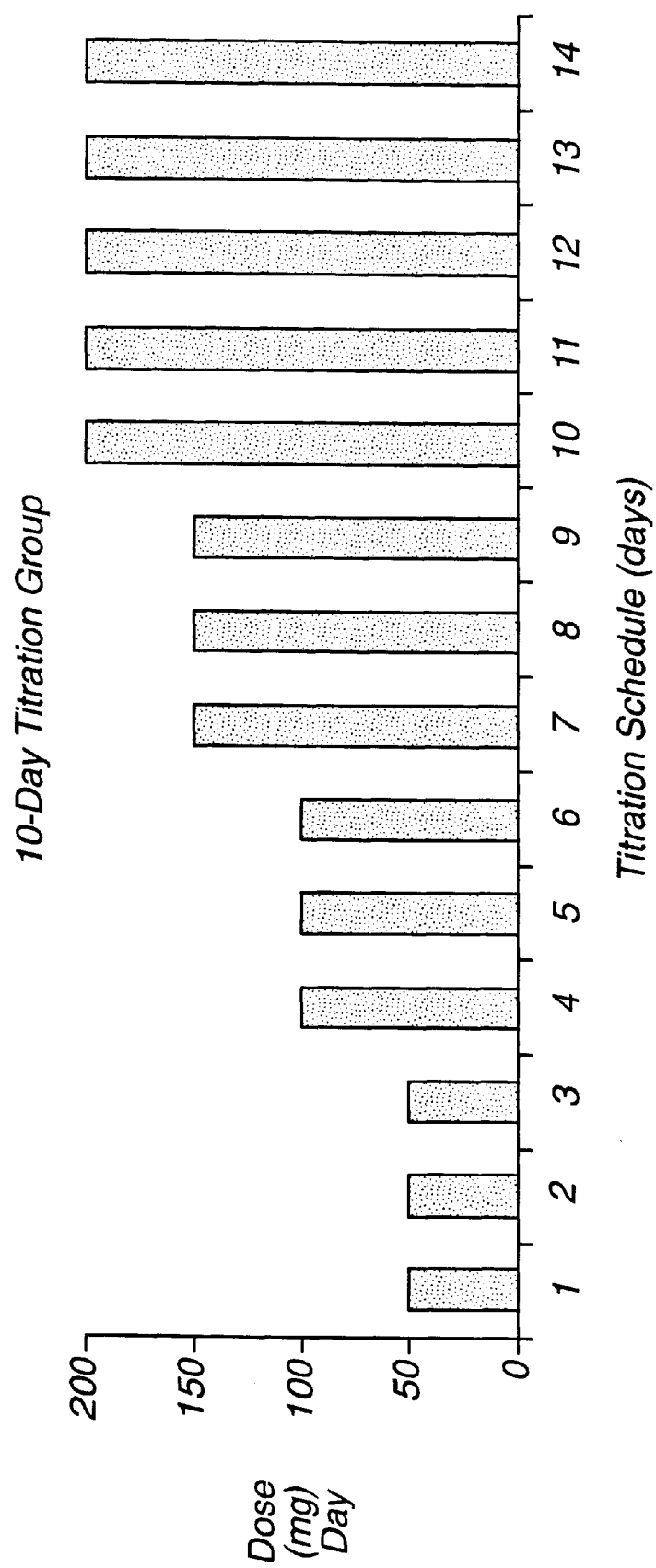

Patients with chronic joint pain who had been receiving a maintenance dose (±25%) of NSAID for at least 30 days, and who required additional pain relief, were randomized into three titration groups and a placebo group using a 2:2:2:1 randomization schedule. Double-blind therapy began on Day 1, with patients receiving either placebo or one of three titration regimens, ultimately reaching the study target dose of 200 mg/day of tramadol in either 1 day, 4 days (increasing by 50 mg increments each day; FIGS. 1a, 1b and 1c), or 10 days (increasing by 50 mg increments every 3 days) Patients continued to take their stable dose of NSAID throughout the double-blind phase, in addition to the study drug or placebo. On Day 14, all patients underwent a physical examination with clinical laboratory tests, as well as adverse event assessment Patients could be discontinued from the study as the result of adverse events, treatment failure, significant protocol violation, development of an intercurrent illness or at their own request.

Patients were randomly assigned according to a central computer-generated schedule to receive placebo or one of three tramadol dosage regimens that involved either a 1-, 4- or 10-day titration schedule to attain the study target dose of 200 mg/day. Study medication or placebo was administered four times a day using a double-dummy technique to ensure blinding throughout the full titration schedule. Medication distribution was blinded and controlled through the use of blister packs which contained medication with the appropriate number of active tablets and placebos for the 14-day study period, plus 2 additional days of therapy. Three hundred and fifty-two (352) patients completed the study. Reasons leading to discontinuation included adverse events, lack of drug effectiveness, intercurrent illness, protocol violation and patient choice.

The results of the study showed that a slower initial titration of tramadol is effective in reducing discontinuations due to all adverse effects and, in particular, dizziness and nausea.

Among the three tramadol titration groups, patients in the 10-day titration group experienced the fewest discontinuations due to dizziness and/or vertigo, nausea and/or vomiting, and any other adverse event. The 10-day titration rate was statistically significantly different (<0.05) from both the 1-day rate and the 4-day rate for discontinuations due to dizziness and/or vertigo and any other adverse event. The study demonstrated that a slower rate of initiation of tramadol therapy (i.e. 50 mg increments every 3 days) will result in improved tolerability because of significantly fewer discontinuations due the occurrence of adverse events.

EXAMPLE 2

Tramadol, in the form of its hydrochloride salt, was studied in a multicenter, outpatient, randomized, double-blind parallel study comprised of two phases: a screening/open-label run-in study and a double-blind phase. Subjects with chronic pain (e.g. musculoskeletal, neuropathic, joint etc.) for at least three months prior to the study, who had been receiving a daily NSAID dose for at least 30 days prior to the study, who required additional relief of their chronic pain, and who completed the screening evaluations were enrolled in the open-label phase on Day 0 and began open-label study medication on Day 1. Tramadol hydrochloride was titrated in 50 mg/day increments to 200 mg/day over four days. Subjects continued on the 200 mg/day dosage for up to an additional 10 days.

Subjects who experienced nausea and/or vomiting within the 14-day open-label period severe enough for the subjects to discontinue tramadol hydrochloride treatment had the opportunity to enter the double-blind phase. Approximately 150 adult male and female subjects who discontinued the open-label phase due to nausea and/or vomiting were randomized in the double-blind phase to one of three tramadol hydrochloride treatment regimens. Subjects who entered the double-blind phase were assigned in an even-distribution, randomized, double-blind fashion to one of three treatment regimens 10 days after discontinuing open-label tramadol hydrochloride. Subjects were randomized on Day 0 and began double-blind therapy on Day 1 with one of three dosage regimens of tramadol hydrochloride that employed either a 10-, 16- or 13-day titration schedule in order to achieve a maximum dose of either 200 mg/day for the 10- and 16-day regimen or 150 mg/day for the 13-day regimen. On Days 1–28, the subjects took double-blind study medication consisting of either 25 mg of tramadol hydrochloride or matching placebo (two capsules q.i.d.). The three tramadol hydrochloride dosage regimens were designed to achieve a maximum dose (200 mg/day or 150 mg/day) at different rates of titration (10-, 16- or 13-day).

Subjects assigned to the 10-day titration group received tramadol hydrochloride at 50 mg q.d. on Days 1–3, 50 mg b.i.d. on Days 4–6, 50 mg t.i.d. on Days 7–9 and 50 mg q.i.d. on Days 10–28; subjects assigned to the 16-day titration group received tramadol hydrochloride at 25 mg q.d. on Days 1–3, 25 mg b.i.d. on Days 4–6, 25 mg t.i.d. on Days 7–9, 25 mg q.i.d. on Days 10–12, 50 mg t.i.d. on Days 13–15 and 50 mg q.i.d. on Days 16–28; and subjects assigned to the 13-day titration group received tramadol hydrochloride at 25 mg q.d. on Days 1–3, 25 mg b.i.d. on Days 4–6, 25 mg t.i.d. on Days 7–9, 25 mg q.i.d. on Days 10–12, and 50 mg t.i.d. on Days 13–28. Subjects who did not experience nausea and/or vomiting severe enough to discontinue tramadol hydrochloride treatment by the end of the open-label run-in phase were discontinued from the study. Subjects continued taking their daily dose of NSAID throughout both the open-label/run-in and double-blind phases of the study. At the completion of the double-blind phase or at the time of premature discontinuation, subjects returned to the invesitgational site for follow-up efficacy and safety evaluations.

Efficacy evaluations were performed at all visits. These evaluations included a subject assessment of pain using a 10 cm pain visual analogue (PVA) scale and overall assessments of the study medication made by the subject and the investigator. Safety evaluations were performed at screening, at the end of the open-label/run-in phase and at the end of the double-blind phase and included assessments of the occurrence of adverse events, vital signs and body weight measurements and physical examinations.

Analyses and summaries were performed for all subjects who discontinued the screening/open-label/run-in phase due to nausea and/or vomiting, who were then randomized to one of the three double-blind titration groups, who took at least one dose of the study medication, and who provided post baseline information. Subjects who participated in the open-label/run-in phase but who either did not qualify for or chose not to participate in the double-blind group are included only in the overall accounting of subjects entering the open-label/run-in phase.

A total of 931 subjects were enrolled in the study at 29 centers for the open-label/run-in phase. There were no apparent differences between the non-randomized and randomized population in terms of the demographic attributes of race, age, chronic painful condition, or time since diagnosis; however, a slightly higher percentage of women were randomized into the double-blind phase of the study. Osteoarthritis and chronic low-back syndrome were the most common chronic painful conditions reported for the overall population (29.3% and 28.8% of subjects, respectively).

The primary analysis group included 167 subjects, including 54, 59 and 54 subjects in the tramadol hydrochloride treatment groups that employed 10-, 16- and 13-day titration periods, respectively. Chronic low-back syndrome and osteoarthritis were the most common chronic painful conditions reported for the overall population (each represented 28.1% of subjects). The relative proportions of other chronic painful conditions varied somewhat across treatment groups.

The mean reduction from baseline PVA scores for subjects in the open-label/run-in phase was 2.1 cm. In the double-blind phase, the mean reduction from baseline PVA scores was highest in the 13-day tramadol hydrochloride titration group (1.6 cm), followed by the 16-day titration group (1.5 cm); and the 10-day titration group (1.4 cm).

Figure 2:
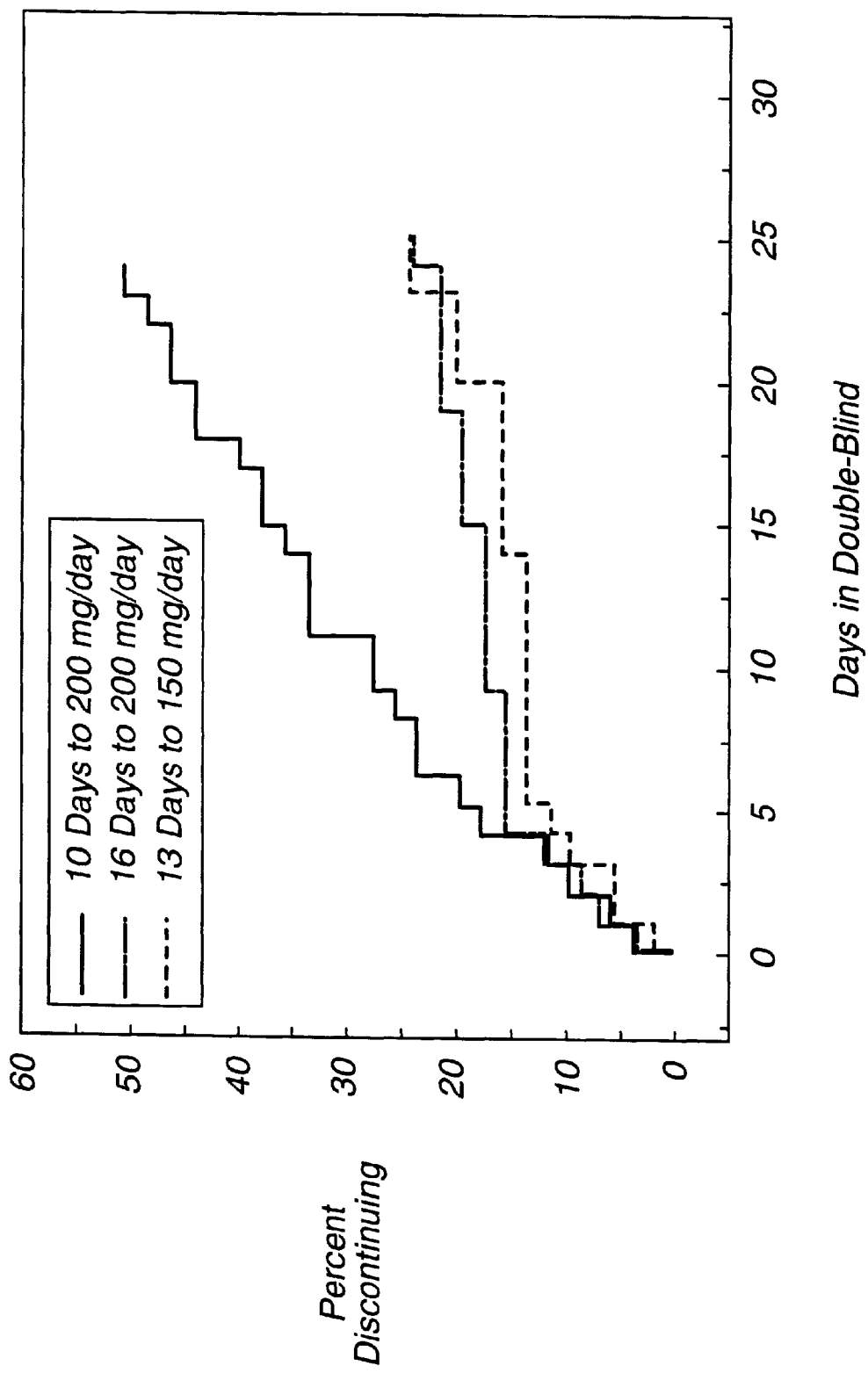

The pairwise log-rank test revealed statistically significant differences (p=0.006) between the Kaplan-Meier survival curve of the 10-day titration group and the survival curves of both the 16-day (p=0.007) and the 13-day titration group (p=0.006) with respect to discontinuations from nausea and/or dizziness. The survival curve plots the relationship between the cumulative probability of discontinuation and the length of exposure. Examination of the curves (FIG. 2) shows the cumulative probability of discontinuation due to nausea and/or vomiting in the three titration groups to be similar through the first five days of titration. After day 5, the cumulative probability of discontinuation due to nausea and/or vomiting in the 10-day titration group continues to increase at essentially the same rate as seen in the first five days while the survival curves of the two slower titration groups plateau. The pairwise comparison between the survival curves of the 16-day and 13-day titration groups was not statistically significant (p=0.94).

The median time to discontinuation due to nausea and/or vomiting was shorter for the 16-day tramadol hydrochloride titration group (4.0 days; (FIG. 2) followed by the 13-day group (5.5 days) and the 10-day group (9.0 days).

Figure 3:
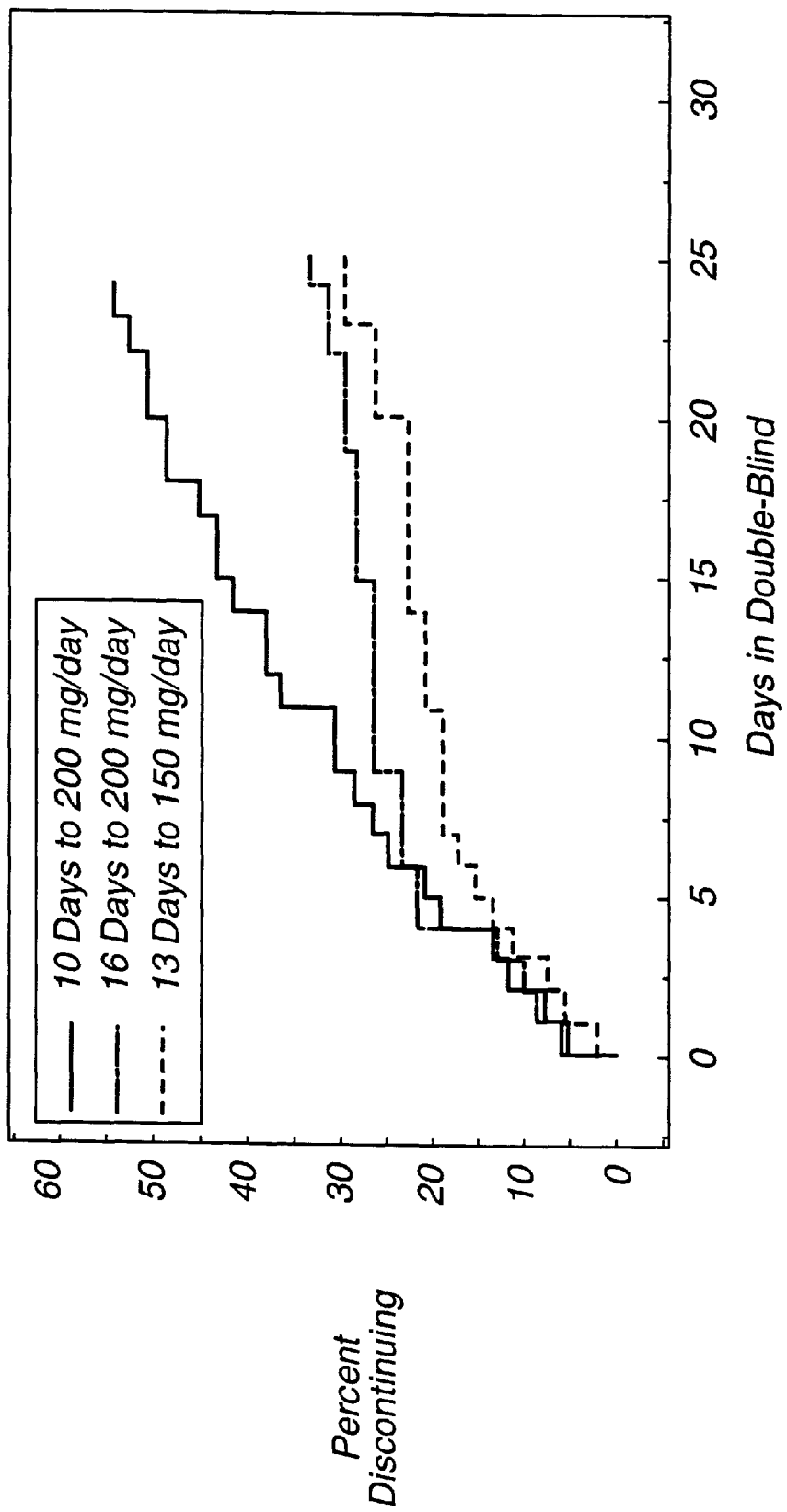

The pairwise log-rank test revealed statistically significant differences between the Kaplan-Meier survival curve of the 10-day titration group and the survival curves of both the 16-day titration group (p=0.030) and the 13-day titration group (p=0.010) with respect to discontinuations because of any adverse effect. The survival curve plots the relationship between the cumulative probability of discontinuation and length of exposure. Examination of the curves (FIG. 3) shows the cumulative probability of discontinuation due to any adverse event in the three titration groups to be similar through the first five days of titration. After day 5, the cumulative probability of discontinuation due to any adverse event in the 10-day and 16-day titration groups continue to increase while the survival curves of the 13-day titration group begins to fall below them. After 10 days of titration, the survival curves of the 16-day and 13 day titration groups begin to plateau while the cumulative probability of discontinuation in the 10-day titration group continues to increase. The pairwise comparison between the survival curves of the 13-day and the 16-day groups was not statistically significant (p=0.620).

The median time to discontinuation due to any adverse event was shorter for the 16-day tramadol hydrochloride titration group (6.0 days; FIG. 5) followed by the 13-day group (6.5 days) and the 10-day group (9.0 days).

The studies demonstrated that a slower initial titration rate of tramadol hydrochloride reduced the incidence of discontinuation due to nausea and/or vomiting in subjects with chronic pain who previously had difficulty tolerating tramadol hydrochloride because of nausea and/or vomiting. This is based on the cumulative proportion of subjects who discontinued due to nausea and/or vomiting, with the group that titrates to 200 mg/day over 10 days showing a 20 percentage advantage over the groups that titrate to 200 mg/day over 16 days.

What is claimed is:

1. A regimen for the treatment of pain which comprises administering to one in need thereof about 25 mg tramadol on days 1–3; about 50 mg of tramadol on days 4–6; about 75 mg of tramadol on days 7–9; about 100 mg of tramadol on days 10–12; about 150 mg of tramadol on days ±3–15; about 200 mg of tramadol on days 16–18 and about 200 mg to about 400 mg of tramadol per day thereafter, in the form of a pharmaceutical composition containing tramadol as the active ingredient; whereby discontinuations due to adverse side effects are reduced.

2. A regimen for the treatment of pain which comprises administering to one in need thereof about 25 mg tramadol on days 1–3; about 50 mg of tramadol on days 4–6; about 75 mg of tramadol on days 7–9; about 100 mg of tramadol on days 10–12; about 150 mg of tramadol on days ±3–15; and about 200 mg on day 16, in the form of a pharmaceutical composition containing tramadol as the active ingredient; whereby discontinuations due to adverse side effects are reduced.

3. A regimen for the treatment of pain which comprises administering to one in need thereof about 25 mg of tramadol on days 1–3; about 50 mg of tramadol on days 4–6; about 75 mg of tramadol on days 7–9; about 100 mg of tramadol on days 10–12; about 150 mg of tramadol on days 13–15; and about 200 mg on days 16–18, in the form of a pharmaceutical composition containing tramadol as the active ingredient; whereby discontinuations due to adverse side effects are reduced.

4. A regimen for the treatment of pain which comprises administering to one in need thereof about 25 mg tramadol on days 1–3; about 50 mg of tramadol on days 4–6; about 75 mg of tramadol on days 7–9; about 100 mg of tramadol on days 10–12, in the form of a pharmaceutical composition containing tramadol as the active ingredient; whereby discontinuations due to adverse side effects are reduced.

5. The regimen the treatment of pain according to claim 2 which comprises administering to for in need thereof about 25 mg of tramadol q.d. on days 1–3, about 25 of mg of tramadol b.i.d. on days 4–6, about 25 mg of tramadol t.i.d. on days 7–9, about 25 mg of tramadol q.i.d. on days 10–12, and about 50 mg of tramadol t.i.d. on days 13–15, and about 50 mg of tramadol q.i.d. on day 16, in the form of a pharmaceutical composition containing tramadol as the active ingredient; whereby discontinuations due to adverse side effects are reduced.

6. The regimen for the treatment of pain according to claim 2 which comprises administering to one in need thereof about 25 mg of tramadol q.d. on days 1–3, about 25 of mg of tramadol b.i.d. on days 4–6, about 25 mg of tramadol t.i.d. on days 79, about 25 mg of tramadol q.i.d. on days 10–12, and about 50 mg of tramadol t.i.d. on days 13–15, and about 50 mg of tramadol q.i.d. on days 16–18, in the form of a pharmaceutical composition containing tramadol as the active ingredient; whereby discontinuations due to adverse side effects are reduced.

7. The regimen for the treatment of pain according to claim 1, which comprises administering to one in need thereof about 25 mg of tramadol q.d. on days 1–3, about 25 of mg of tramadol b.i.d. on days 4–6, about 25 mg of tramadol t.i.d. on days 7–9, about 25 mg of tramadol q.i.d. on days 10–12, and about 50 mg of tramadol t.i.d. on days 13–15, about 50 mg of tramadol q.i.d. on days 16–18 and about 50–100 mg of tramadol q.i.d. thereafter, in the form of a pharmaceutical composition containing tramadol as the active ingredient; whereby discontinuations due to adverse side effects are reduced.

8. The regimen for the treatment of pain according to claim 4, which comprises administering to on in need thereof about 25 mg of tramadol q.d. on days 1–3, about 25 of mg of tramadol b.i.d. on days 4–6, about 25 mg of tramadol t.i.d. on days 7–9, about 25 mg of tramadol q.i.d. on days 10–12, in the form of a pharmaceutical composition containing tramadol as the active ingredient; whereby discontinuations due to adverse side effects are reduced.

9. A regimen for the treatment of pain which comprises administering to one in need thereof about 25 mg tramadol on days 1–3; about 50 mg of tramadol on days 4–6; about 75 mg of tramadol on days 7–9; about 100 mg of tramadol on days 10–12; about 150 mg of tramadol on days 13–15, in the form of a pharmaceutical composition containing tramadol as the active ingredient; whereby discontinuations due to adverse side effects are reduced.

10. A regimen for the treatment of pain which comprises administering to one in need thereof about 25 mg tramadol on days 1–3; about 50 mg of tramadol on days 4–6; about 75 mg of tramadol on days 7–9; about 100 mg of tramadol on days 10–12; about 150 mg of tramadol on days 13–15, and thereafter, in the form of a pharmaceutical composition containing tramadol as the active ingredient; whereby discontinuations due to adverse side effects are reduced.

11. The regimen or the treatment of pain according to claim 10, which comprises administering to one in need thereof about 25 mg of tramadol q.d. on days 1–3, about 25 of mg of tramadol t.i.d. on days 4–6, about 25 mg of tramadol t.i.d. on days 7–9, about 25 mg of tramadol q.i.d. on days 10–12, and about 50 mg of tramadol t.i.d. on days 13–15 and thereafter, in the form of a pharmaceutical composition containing tramadol as the active ingredient; whereby discontinuations due to adverse side effects are reduced.

* * * * *